United States Patent
Etienne et al.

(10) Patent No.: US 9,447,001 B2
(45) Date of Patent: Sep. 20, 2016

(54) PROCESS AND DEVICE FOR SIMULATED-COUNTERCURRENT CHROMATOGRAPHIC SEPARATION FOR THE PRODUCTION OF METAXYLENE WITH HIGH YIELD

(71) Applicant: IFP Energies nouvelles, Rueil-Malmaison Cedex (FR)

(72) Inventors: Pascal Etienne, Estrablin (FR); Philibert Leflaive, Mions (FR); Damien Leinekugel Le Cocq, Lyons (FR); Catherine Laroche, Vernaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 381 days.

(21) Appl. No.: 14/095,404

(22) Filed: Dec. 3, 2013

(65) Prior Publication Data

US 2014/0155673 A1    Jun. 5, 2014

(30) Foreign Application Priority Data

Dec. 3, 2012  (FR) ...................................... 12 03278

(51) Int. Cl.
| | | |
|---|---|---|
| *C07C 7/12* | (2006.01) | |
| *C07C 7/13* | (2006.01) | |
| *B01D 15/18* | (2006.01) | |
| *B01J 20/18* | (2006.01) | |
| *B01J 20/28* | (2006.01) | |

(52) U.S. Cl.
CPC ............. *C07C 7/13* (2013.01); *B01D 15/1828* (2013.01); *B01D 15/1842* (2013.01); *B01J 20/186* (2013.01); *B01J 20/2803* (2013.01); *B01J 20/28011* (2013.01)

(58) Field of Classification Search
CPC .................................. C07C 7/12; C07C 7/13
USPC ........................................ 585/828, 827, 825
See application file for complete search history.

(56) References Cited

U.S. PATENT DOCUMENTS

| 6,376,734 B1 | 4/2002 | Magne-Drisch et al. |
| 7,812,208 B2 | 10/2010 | Cheng et al. |
| 2010/0076243 A1 | 3/2010 | Cheng et al. |
| 2013/0053610 A1 | 2/2013 | Leinekugel Le Cocq et al. |

FOREIGN PATENT DOCUMENTS

| FR | 2693186 A1 | 1/1994 |
| FR | 2795407 A1 | 12/2000 |
| FR | 2979252 A1 | 3/2013 |

OTHER PUBLICATIONS

Search Report for FR1203278 dated Jul. 24, 2013.
Inst Francais Du Petrole, "Sepn. and recovery of para-xylene," Espacenet, Publication Date: Jan. 7, 1994; English Abstract of FR2693186.

*Primary Examiner* — Thuan D Dang
(74) *Attorney, Agent, or Firm* — Millen, White, Zelano and Branigan, P.C.

(57) ABSTRACT

This invention describes a process for separation of xylenes for the purpose of the production of high-purity metaxylene, a simulated countercurrent process using at least one adsorber with a limited cumulative total level (Hcu) of adsorbent at a surface velocity (Vsl) that is less than 2 cm/s.

14 Claims, No Drawings

PROCESS AND DEVICE FOR SIMULATED-COUNTERCURRENT CHROMATOGRAPHIC SEPARATION FOR THE PRODUCTION OF METAXYLENE WITH HIGH YIELD

FIELD OF THE INVENTION

The invention relates to the field of the separation of metaxylene (MX) from a feedstock of aromatic hydrocarbons essentially comprising 8 carbon atoms by contact between liquid and solid phases. With this type of feedstock being able to be separated by distillation only with difficulty, a family of adsorption processes and related devices known under the name of processes or devices of chromatographic separation or "simulated moving bed" or "simulated countercurrent" is then used, which we will designate below by the abbreviation CCS.

The invention relates to a CCS separation process that makes it possible to obtain high-purity MX, or MX of a purity of at least 99.5%, in a single step.

EXAMINATION OF THE PRIOR ART

The CCS separation is well known in the state of the art. As a general rule, a process for separation of metaxylene operating in simulated countercurrent comprises at least four zones, and optionally five or six, each of these zones consisting of a certain number of successive beds, and each zone being defined by its position encompassed between a supply point and a draw-off point.

Typically, a CCS unit for the production of metaxylene is supplied by at least one feedstock F that is to be fractionated (containing metaxylene and the other C8 aromatic isomers) and a desorbent D, sometimes called eluant (generally toluene). At least one raffinate R containing the isomers of metaxylene and desorbent and an extract E containing metaxylene and desorbent are drawn off from said unit.

The supply and draw-off points are modified over time, i.e., offset in the same direction by a value that corresponds to a bed. The movements of the different injection or draw-off points can be either simultaneous or non-simultaneous as the patent FR2785196 teaches. The process according to this second operating mode is called VARICOL.

Conventionally, four different chromatographic zones are defined in a CCS unit.

Zone 1: Zone for desorption of metaxylene, encompassed between the injection of the desorbent D and the sampling of the extract E.

Zone 2: Zone for desorption of metaxylene isomers, encompassed between the sampling of the extract E and the injection of the feedstock that is to be fractionated F.

Zone 3: Zone for adsorption of metaxylene, encompassed between the injection of the feedstock and the draw-off of the raffinate R.

Zone 4: Zone located between the draw-off of raffinate R and the injection of the desorbent D.

The processes for separation of metaxylene by CCS are generally composed of 24 beds distributed in two adsorbers of 12 beds each, with each bed having an adsorbent solid level of approximately 1.1 m. Thus, the cumulative level of adsorbent solid over the entire unit, as will be denoted Hcu below, is approximately 26 m.

Recent research in the field of adsorbents for the separation of metaxylene has made it possible to develop adsorbents with improved transfer properties. For example, the U.S. Pat. No. 7,812,208 discloses a process for separation of metaxylene with an adsorbent that comprises the NaY zeolite having a mean crystal size of between 50 and 700 nanometers. This patent discloses that the process is performed in a simulated moving bed at a temperature that is preferably between 60° C. and 250° C. The description does not provide any information on the implementation of the process (i.e., the number of beds, the sieve quantity used, the size of zones, flow rates, . . . ).

SUMMARY DESCRIPTION OF THE INVENTION

The process according to this invention proposes an improved implementation of the production of high-purity metaxylene by using a cumulative level of adsorbent solid over the entire adsorber(s) (denoted Hcu), lower than the one conventionally used in a 24-bed adsorber, and by performing the process with a mean surface velocity over each adsorber that is between 0.9 cm/s and 1.8 cm/s, the latter being defined as the mean recycling volumetric flow rate at the temperature of the process divided by the area of the cross-section of the adsorber.

It was actually noted, surprisingly enough, that the use of a cumulative level of adsorbent solid over all of the adsorbers (Hcu) encompassed between 6 m and 21 m, combined with a mean surface velocity over each adsorber (Vsl) encompassed between 0.9 cm/s and 1.8 cm/s, made it possible to produce high-purity metaxylene, i.e., MX of a purity of greater than 99.5%, with improved performance levels relative to a conventional use of 24 beds.

The significant reduction of the cumulative level (Hcu) makes it possible in a particular case to operate the unit with a single adsorber, which brings about a significant gain in terms of investments relative to a process composed of two adsorbers.

In a more specific way, this invention can be defined as a process for separation of metaxylene by simulated countercurrent chromatography (CCS) starting from a feedstock F that essentially comprises metaxylene and its C8 aromatic isomers, with said process using a zeolitic adsorbent solid based on Y zeolite crystals and a certain proportion of a non-zeolitic phase, in which the Y zeolite crystals have a mean diameter of a number that is less than or equal to 1.7 µm, preferably less than or equal to 1.5 µm, and preferably also less than or equal to 1.2 µm, a process that is implemented in at least one adsorber that is divided into 4 chromatographic zones that are defined in the following manner:

Zone 1: Zone for desorption of metaxylene, encompassed between the injection of the desorbent D and the sampling of the extract E, Zone 2: Zone for desorption of isomers of metaxylene, encompassed between the sampling of the extract E and the injection of the feedstock that is to be fractionated F, Zone 3: Zone for adsorption of metaxylene, encompassed between the injection of the feedstock and the draw-off of raffinate R, Zone 4: Zone located between the draw-off of raffinate R and the injection of the desorbent D, said process being characterized in that it has a cumulative level of adsorbent solid over all of the adsorbers (Hcu) encompassed between 6 m and 21 m, and in that the mean surface velocity over each adsorber (Vsl) is between 0.9 cm/s and 1.8 cm/s.

According to a preferred variant of the process for separation of xylenes according to the invention, the Si/Al atomic ratio of the adsorbent is preferably such that 2.0<Si/Al<3.0, and preferably such that 2.5≤Si/Al<2.85.

According to another preferred variant of the process for separation of xylenes according to the invention, the adsorbent solid that is used is a zeolitic adsorbent based on NaY or NaLiY crystals with crystals whose mean diameter in numbers is between 0.1 and 1.0 micron and preferably between 0.1 and 0.8 micron.

According to another variant of the process for separation of xylenes according to the invention, the mean distribution over a cycle of the cumulative level (Hcu) of adsorbent solid is as follows:
The cumulative level of adsorbent solid in zone 1, on average over a cycle, is 17%±5% of (Hcu),
The cumulative level of adsorbent solid in zone 2, on average over a cycle, is 41.5%±5% of (Hcu),
The cumulative level of adsorbent solid in zone 3, on average over a cycle, is 25%±5% of (Hcu),
The cumulative level of adsorbent solid in zone 4, on average over a cycle, is 16.5%±5% of (Hcu).

In a preferred manner, the total number of beds is between 6 and 18 beds, and in an even more preferred manner, the total number of beds is between 8 and 15 beds, with the beds all being identical.

According to this invention, the total number of beds can be distributed over one or more adsorbers.

In a preferred manner, the height of a bed is between 0.7 m and 1.40 m.

In a preferred variant, the number of adsorbers used in the process according to this invention is 1.

When there are several adsorbers, the latter are arranged in series in the sense that the 3 following characteristics are observed:
The last bed of the nth adsorber is connected to the first bed of the adsorber n+1, via a line containing at least one recirculation pump and optionally other equipment such as a flowmeter, a pressure sensor, etc.,
The last bed of the last adsorber is connected to the first bed of the first adsorber via a line that contains at least one recirculation pump and optionally other equipment such as a flowmeter, a pressure sensor, etc.,
All of the adsorbers have at least 1 introduction point of the feedstock, 1 introduction point of the eluant, 1 draw-off point of the raffinate, and 1 draw-off point of the extract.

In a preferred manner, the operating conditions of the adsorption stage of the process according to this invention are as follows:
Temperature 100° C. to 250° C., preferably 120° C. to 180° C.,
Pressure between the bubble pressure of the xylenes at the temperature of the process and $30 \times 10^5$ Pa,
Ratio of the flow rate of desorbent to the flow rate of feedstock of between 0.7 and 6.5,
Recycling rate of 3.5 to 14, preferably 4.5 to 12 (with the recycling rate being defined as the ratio between the mean flow rate flowing into the different beds of the adsorber over the feedstock injection flow rate in this adsorber),
Water content in the liquid phase of between 0 and 140 ppm (by weight) and in a preferred manner of between 5 and 120 ppm (by weight).

Finally, according to another preferred variant of the process according to this invention, the fire loss of the adsorbent solid measured at 900° C. is between 0% and 4.0% by weight, and preferably between 0% and 3.0% by weight.

DETAILED DESCRIPTION OF THE INVENTION

This invention relates to a process for separation of metaxylene by simulated countercurrent chromatography (CCS) starting from a feedstock F essentially comprising metaxylene and its C8 aromatic isomers, with said process being implemented in an adsorber and characterized in that it has a cumulative level of adsorbent solid over all of the adsorbers (Hcu) of between 6 and 21 m, and in that the mean surface velocity over each adsorber (Vsl) is between 0.9 and 1.8 cm/s.

A cumulative level of adsorbent solid over all of the adsorbers (Hcu) that is greater than 21 m makes the operation in a single adsorber costly due to pressure drops and size losses of the adsorber.

In addition, the purpose of the process according to the invention is to deal with the high flow rates of the feedstock to be treated, making it necessary to have an inside diameter of each adsorber of between 4 m and 10 m.

A cumulative level of adsorbent solid over all of the adsorbers (Hcu) that is less than 6 m poses liquid distribution problems.

Furthermore, a low linear surface velocity (Vsl) (i.e., less than 0.9 cm/s) generally does not make it possible to obtain a high yield and is likely to cause distribution problems, in particular for large-diameter adsorbers.

Conversely, a surface velocity (Vsl) that is higher than 1.8 cm/s can bring about a movement of the adsorbent on the surface of the beds that has a negative effect on performance levels and that can cause attrition of the latter.

In a preferred manner, the adsorbent of the process according to the invention is a zeolitic adsorbent based on NaY or NaLiY zeolite crystals in which the Y zeolite crystals have a mean diameter in numbers of a number that is less than or equal to 1.7 μm, preferably less than or equal to 1.5 μm, and more preferably less than or equal to 1.2 μm.

In a preferred manner, the process according to this invention uses an adsorbent solid that is a zeolitic adsorbent based on NaY or NaLiY crystals with crystals whose mean diameter in numbers is between 0.1 and 1.0 micron, and preferably between 0.1 and 0.8 micron.

The Si/Al atomic ratio of the adsorbent is preferably such that 2<Si/Al<3 and preferably such that 2.5≤Si/Al<2.85.

The estimation of the mean diameter in numbers of Y zeolite crystals contained in the adsorbent is done by observation with a scanning electron microscope (SEM) on a polished cross-section in back-scattered electrons mode, with chemical contrast.

So as to estimate the size of the zeolite crystals on the samples, a set of pictures with a magnification of at least 5,000 is made. Next, the diameter of at least 200 crystals is measured using dedicated software (Smile View, LoGraMi).

The mean diameter in numbers is next calculated starting from the granulometric distribution by applying the standard ISO 9276-2:2001 (representation of data obtained by granulometric analysis—Part 2: Calculation of mean sizes/diameters of particles and moments from granulometric distributions). In the document cited, the term "mean diameter in numbers" is used that we will retain with the same meaning within the framework of this invention.

The process for separation of metaxylene according to the invention can use an adsorbent containing a large fraction of binder (i.e., typically between 10 and 25%), but also an adsorbent without a binder (called "binderless" in English parlance), i.e., containing a quantity of amorphous phase that is typically less than 1%, or an adsorbent containing a reduced binder content (called "binder-low" in English parlance), i.e., containing a quantity of amorphous phase that is typically between 1 and 5%. These last two types of adsorbents can be obtained in particular after a stage of zeolitization of the binder.

The fire loss measured at 900° C. is between 0% (anhydrous product) and 4% by weight, and preferably between 0% and 3% by weight.

The preferred desorbent is toluene; however, other desorbents, such as benzene, indane or teralin, by themselves or in a mixture, may also be suitable.

In this invention, toluene is preferred due to the ease with which it can be recovered by distillation and for its strong affinity for the adsorbent.

According to another characteristic of the process, the operating conditions of the adsorption stage are as follows:
  Temperature 100° C. to 250° C., preferably 120° C. to 180° C.
  Pressure between the bubble pressure of xylenes at the temperature of the process and $30 \times 10^5$ Pa
  Ratio of the flow rate of desorbent to the flow rate of feedstock of between 0.7 and 6.5
  Recycling rate of 3.5 to 14, preferably 4.5 to 12, with the recycling rate being defined as the ratio between the mean flow rate flowing into the different beds of the adsorber to the feedstock injection flow rate in this adsorber
  Water content in a liquid phase of between 0 and 140 ppm (by weight) and in a preferred manner between 5 and 120 ppm (by weight).

The total number of beds of the process according to the invention is preferably between 6 and 18 beds and in an even more preferred manner between 8 and 15 beds. The number of beds is adjusted in such a way that each bed preferably has a height of between 0.70 m and 1.40 m.

The process according to this invention can make use of one or more adsorbers connected in series. In a preferred manner, the number of adsorbers used is one.

Each adsorber is divided into four chromatographic zones that are defined in the following manner:
  Zone 1: Zone for desorption of metaxylene, encompassed between the injection of desorbent D and the sampling of extract E,
  Zone 2: Zone for desorption of the isomers of metaxylene, encompassed between the sampling of the extract E and the injection of the feedstock that is to be fractionated F,
  Zone 3: Zone for adsorption of metaxylene, encompassed between the injection of the feedstock and the draw-off of the raffinate R,
  Zone 4: Zone located between the draw-off of the raffinate R and the injection of the desorbent D.

According to another characteristic of the process according to the invention, the mean distribution over a cycle of the cumulative level of adsorbent solid is as follows:
  The cumulative level of adsorbent solid in zone 1, on average over a cycle, is 17%±5% of Hcu,
  The cumulative level of adsorbent solid in zone 2, on average over a cycle, is 41.5%±5% of Hcu,
  The cumulative level of adsorbent solid in zone 3, on average over a cycle, is 25%±5% of Hcu,
  The cumulative level of adsorbent solid in zone 4, on average over a cycle, is 16.5%±5% of Hcu.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding FR application No. 12/03.278, filed Dec. 3, 2012, are incorporated by reference herein.

EXAMPLES ACCORDING TO THE INVENTION

The invention will be better understood from reading the two examples that follow.

Example 1

Process According to the Prior Art

A CCS adsorber that consists of 24 beds, with a length of 1.1 m and an inside radius of 1.85 m, with an injection of feedstock, an injection of desorbent, an extract draw-off and a raffinate draw-off, is considered. The adsorbent that is used is an NaY-type zeolitic solid that forms crystals of 0.8 µm shaped in balls of 0.53 mm.

The desorbent is toluene.

The temperature is 160° C., and the pressure is 10 bar. The water content in the extract is 2 ppm (by weight).

The feedstock consists of 20% paraxylene, 22% orthoxylene, 48% metaxylene, and 10% ethylbenzene.

The CCS adsorber consists of 24 beds distributed over two adsorbers, with the beds being separated by distributor plates.

An injection network and a draw-off network correspond to each distributor plate.

The rinsing device that is used is the device with a modulated derivation fluid flow, as described in the patent WO 2010/020715. The synchronicity is 100% in each zone.

The movements of the different injection points or draw-off points are simultaneous. The beds are distributed in 4 chromatographic zones according to the configuration: 4/10/6/4.

The injection flow rates of feedstock and desorbent (defined by considering a reference temperature of 40° C.) are the following:
  0.935 $m^3 \cdot min^{-1}$ for the feedstock,
  4.353 $m^3 \cdot min^{-1}$ for the desorbent.

The extract draw-off flow rate is 3,274 $m^3 \cdot min^{-1}$. The switching period that is used is 53.5 seconds.

The mean surface velocity over the entire adsorber is 1.83 $cm \cdot s^{-1}$.

A purity of metaxylene of 99.50% and a metaxylene yield of 97.61% with a productivity of 66.9 $kg_{MX} \cdot h^{-1} \cdot m^{-3}$ are obtained by simulation.

Example 2

Process According to the Invention

A CCS adsorber that consists of 14 beds distributed over an adsorber is considered, with each bed having a length of 1.1 m, or an Hcu of 15.4 m, and with an inside radius of 1.85 m, with an injection of feedstock, an injection of desorbent, an extract draw-off, and a raffinate draw-off.

The adsorbent that is used is an NaY-type zeolitic solid that forms crystals of 0.8 µm shaped in balls of 0.53 mm.

The desorbent is toluene. The adsorbent and the desorbent are therefore identical to those of the example according to the prior art.

The temperature is 160° C., and the pressure is 10 bar. The water content in the extract is 2 ppm (by weight).

The feedstock consists of 20% paraxylene, 22% orthoxylene, 48% metaxylene, and 10% ethylbenzene.

The CCS adsorber consists of 14 beds separated by distributor plates. An injection network and a draw-off network correspond to each distributor plate.

The rinsing device that is used is the device with a modulated derivation fluid flow, as described in the patent WO 2010/020715. The synchronicity is 100% in each zone.

The movements of the different injection points or draw-off points are not simultaneous. The beds are distributed in 4 chromatographic zones according to the configuration: 2/6/3.5/2.5.

The distribution of the beds is therefore the following during a period (assuming that the beginning and the end of a period are defined by the movement of the desorbent injection point):

From the beginning of the period up to 33.55 seconds (defined relative to the beginning of the period), there are:
    2 beds in zone 1 (between the injection of desorbent D and the draw-off of extract E);
    6 beds in zone 2 (between the draw-off of extract E and the injection of feedstock F);
    3 beds in zone 3 (between the injection of feedstock F and the draw-off of raffinate R);
    3 beds in zone 4 (between the draw-off of raffinate R and the injection of desorbent D);
From 33.55 seconds (defined relative to the beginning of the period) up to the end of the period, there are:
    2 beds in zone 1 (between the injection of desorbent D and the draw-off of extract E);
    6 beds in zone 2 (between the draw-off of extract E and the injection of feedstock F);
    4 beds in zone 3 (between the injection of feedstock F and the draw-off of raffinate R);
    2 beds in zone 4 (between the draw-off of raffinate R and the injection of desorbent D).

The flow rates for injection of feedstock and desorbent (defined by considering a reference temperature of 40° C.) are as follows:
    0.546 m$^3 \cdot$min$^{-1}$ for the feedstock,
    2.539 m$^3 \cdot$min$^{-1}$ for the desorbent.

The extract draw-off flow rate is 1.910 m$^3 \cdot$min$^{-1}$. The switching period that is used is 67.1 seconds.

The mean surface velocity over the entire adsorber is 1.06 cm$\cdot$s$^{-1}$.

By simulation, a metaxylene purity of 99.52% and a metaxylene yield of 97.95% with a productivity of 67.1 kg$_{MX} \cdot$h$^{-1} \cdot$m$^{-3}$ are obtained.

The gain in purity, yield and productivity of metaxylene is therefore significant relative to the prior art.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for separation of metaxylene by simulated countercurrent chromatography (CCS) starting from a feedstock F that comprises metaxylene and its C8 aromatic isomers, said process comprising contacting said metaxylene and C8 aromatic isomers with a zeolitic adsorbent solid based on Y zeolite crystals and a non-zeolitic phase, in which the Y zeolite crystals have a mean diameter of a number that is less than or equal to 1.7 μm in which process at least one adsorber is divided into 4 chromatographic zones that are defined in the following manner:
    Zone 1: a zone desorbing metaxylene, encompassed between injection of a desorbent D and sampling of an extract E,
    Zone 2: a zone desorbing isomers of metaxylene, encompassed between the sampling of the extract E and injection of a feedstock F that is to be fractionated,
    Zone 3: a zone desorbing metaxylene, encompassed between injection of the feedstock and draw-off of a raffinate R,
    Zone 4: a zone located between the draw-off of raffinate R and the injection of the desorbent D,
    with the number of beds of each adsorber being between 6 and 18 beds with the beds all being identical, and the height of each bed being between 0.7 m and 1.40 m, wherein in said process the adsorber(s) have a cumulative level (Hcu) of adsorbent solid of between 6 m and 21 m, a mean surface velocity over each adsorber (Vsl) between 0.9 cm/s and 1.8 cm/s, with said surface velocity being defined as the volumetric flow rate of mean recycling at the temperature of the process that is divided by the area of the cross-section of the adsorber and the cumulative height (Hcu) of adsorbent solid being distributed in the following manner:
    the cumulative level of adsorbent solid in zone 1, on average over a cycle, is 17%±5% of (Hcu),
    the cumulative level of adsorbent solid in zone 2, on average over a cycle, is 41.5%±5% of (Hcu),
    the cumulative level of adsorbent solid in zone 3, on average over a cycle, is 25%±5% of (Hcu),
    the cumulative level of adsorbent solid in zone 4, on average over a cycle, is 16.5%±5% of (Hcu).

2. The process for separation of xylenes according to claim 1, wherein the Si/Al atomic ratio of the adsorbent is such that 2.0<Si/Al<3.0.

3. The process for separation of xylenes according to claim 1, wherein the adsorbent solid that is used is a zeolitic adsorbent based on NaY or NaLiY crystals with crystals whose mean diameter in numbers is between 0.1 and 1.0 micron.

4. The process for separation, of metaxylene according to claim 1, wherein the inside diameter of each adsorber is between 4 m and 10 m.

5. The process for separation of metaxylene according to claim 1, wherein the number of adsorbers used is 1.

6. The process for separation of metaxylene according to claim 1, wherein the operating conditions of the adsorption stage are as follows:
    temperature 100° C. to 250° C.,
    pressure between bubble pressure of the xylenes at the temperature of the process 30×10$^5$ Pa,
    ratio of flow rate of desorbent to flow rate of feedstock of between 0.7 and 6.5,
    recycling rate of 3.5 to 14, with the recycling rate being defined as the ratio between mean flow rate flowing into the different beds of an adsorber to feedstock injection flow rate in said adsorber, and water content in liquid phase of between 0 and 140 ppm (by weight).

7. The process according to claim 1, wherein fire loss of the adsorbent solid that is measured at 900° C. is between 0% and 4.0% by weight.

8. The process according to claim 1, wherein the Y zeolite crystals have a mean diameter less than or equal to 1.5 μm.

9. The process according to claim 1, wherein the Y zeolite crystals have a mean diameter less than or equal to 1.2 μm.

10. The process according to claim 1, wherein the number of beds is between 8 and 15.

11. The process according to claim 1, wherein the Si/Al atomic ratio of the adsorbent is 2.5≤Si/Al<2.85.

12. The process for separation of xylenes according to claim 1, wherein the adsorbent solid that is used is a zeolitic adsorbent based on NaY or NaLiY crystals with crystals whose mean diameter in numbers is between 0.1 and 0.8 micron.

13. The process according to claim 6, wherein the temperature is 120° C. to 180° C., the recycling rate is 4.5 to 12, and the water content in the liquid phase is between 5 and 120 ppm by weight.

14. The process according to claim 1, wherein the five loss of the adsorbent solid that is measured at 900° C. is between 0 and 3.0% by weight.

* * * * *